(12) United States Patent
Hirai

(10) Patent No.: US 7,794,966 B2
(45) Date of Patent: Sep. 14, 2010

(54) METHOD OF MEASURING GLYCATED AMINE

(75) Inventor: Kaoru Hirai, Kyoto (JP)

(73) Assignee: Arkray, Inc., Kyoto (JP)

( * ) Notice: Subject to any disclaimer, the term of this patent is extended or adjusted under 35 U.S.C. 154(b) by 711 days.

(21) Appl. No.: 10/575,214

(22) PCT Filed: Dec. 10, 2004

(86) PCT No.: PCT/JP2004/018503

§ 371 (c)(1),
(2), (4) Date: Apr. 10, 2006

(87) PCT Pub. No.: WO2005/056823

PCT Pub. Date: Jun. 23, 2005

(65) Prior Publication Data

US 2007/0134754 A1    Jun. 14, 2007

(30) Foreign Application Priority Data

Dec. 12, 2003    (JP) .............................. 2003-415304

(51) Int. Cl.
*C12Q 1/26* (2006.01)
*C12Q 1/37* (2006.01)
*G01N 33/92* (2006.01)

(52) U.S. Cl. .............................. 435/25; 435/23; 435/8; 435/220; 435/191

(58) Field of Classification Search .................... None
See application file for complete search history.

(56) References Cited

U.S. PATENT DOCUMENTS

| 5,712,138 | A | 1/1998 | Kato et al. |
| 5,789,221 | A | 8/1998 | Kato et al. |
| 5,824,527 | A | 10/1998 | Kato et al. |
| 2002/0025546 | A1 * | 2/2002 | Komori et al. ................. 435/28 |
| 2003/0186346 | A1 | 10/2003 | Yagi et al. |
| 2004/0209378 | A1 | 10/2004 | Horii et al. |
| 2004/0248226 | A1 | 12/2004 | Yonehara et al. |

FOREIGN PATENT DOCUMENTS

| EP | 1 002 874 | 5/2000 |
| EP | 1 304 385 | 4/2003 |
| EP | 1 329 722 | 7/2003 |
| EP | 1443115 A1 * | 8/2004 |
| EP | 1 477 569 | 11/2004 |
| JP | 7-289253 | 11/1995 |
| JP | 8-154672 | 6/1996 |
| JP | 8-336386 | 12/1996 |
| JP | 2000-97927 | 4/2000 |
| JP | 2000-180439 | 6/2000 |
| JP | 2000-333696 | 12/2000 |
| WO | 99/20039 | 4/1999 |
| WO | 03/033729 | 4/2003 |
| WO | 03/033730 | 4/2003 |

OTHER PUBLICATIONS

English machine-translation of WO 2003/033729, published on Apr. 23, 2003 in Japanese.*
Fujiwara, et al., "Conversion of Substrate Specificity of Glycated Amino Acid Oxidase Derived from *Fusarium oxysporum*", Annual Meeting 2000, The Society for Biotechnology, Japan, 2000.
Examiner of JPO—Harue Tanaka, Japanese Office Action issued in corresponding Japanese Application No. 2005-516199, mailed Jan. 26, 2010 with its English Translation—7 pages.

* cited by examiner

*Primary Examiner*—Lisa J Hobbs
(74) *Attorney, Agent, or Firm*—Hamre, Schumann, Mueller & Larson, P.C.

(57) ABSTRACT

The present invention aims to enable highly reliable measurement of a glycated amine. A fructosyl amino acid oxidase (FAOD) is added to a sample to remove a non-analyte glycated amine that is present in the sample and different from an analyte glycated amine. Thereafter, a protease is added to the sample to degrade the analyte glycated amine, and the degradation product of the analyte glycated amine reacts with the FAOD that has already been added to the sample. By measuring this redox reaction, the amount of the analyte glycated amine can be measured.

21 Claims, No Drawings

METHOD OF MEASURING GLYCATED AMINE

TECHNICAL FIELD

The present invention relates to a method of measuring a glycated amine such as a glycated protein using a redox reaction.

BACKGROUND ART

Glycated hemoglobin (in particular, "HbA1c") present in blood cells serves as a significant indicator in the diagnosis, therapy, etc. of diabetes because the concentration thereof reflects the patient's past history of blood glucose levels. In general, HbA1c is measured by an immunoassay, HPLC, or the like.

However, in whole blood or blood cells, not only glycated hemoglobin (glycated Hb) as an analyte but also various glycation products such as glycated amines (e.g., glycated albumins, glycated peptides, and glycated amino acids) are present as non-analytes. Thus, there has been a problem in that the glycation products (the non-analytes) other than the analyte also are measured, so that the measured value becomes greater than the true value or a false positive result is obtained In order to solve such a problem, in the field of immunoassay, the following methods have been proposed, for example. That is, a method has been proposed in which, before causing a main reaction between glycated Hb as an analyte and an antibody against the analyte, a complex of a non-analyte with an antibody against the non-analyte is formed so that the structure of the non-analyte is changed to that causing no influence on the immunoreaction of the glycated Hb (see Patent Document 1, for example), and a method has been proposed in which a non-analyte is separated and removed from a sample by B/F separation. On the other hand, in the field of HPLC, a method has been proposed in which two HPLC columns are provided for one sample so that a non-analyte is removed from the sample in the first column and an analyte is separated and analyzed in the second column, for example.

However, the above-described immunoassays have a problem in that they require a high cost and besides, an antigen-antibody reaction other than the main reaction needs to be performed further, which complicates the environment setting of the reaction system and causes the measurement to take a long time. Furthermore, with regard to the immunoassay using the B/F separation, it is obvious that the operation is complicated. Still further, because an antibody only acts on a substance (an antigen) that exhibits specificity to the antibody, when the type of a non-analyte contained in the sample is unknown or many types of non-analytes are contained in the sample, it is difficult to remove the influence of the non-analyte(s) sufficiently. Moreover, according to the above-described HPLC, a cost increase cannot be avoided because it uses two columns. Besides, the separation of the non-analyte takes a long time, so that, when the improvement in the measurement accuracy is intended, there is a limit to the reduction in the measurement period.

On the other hand, in recent years, enzymatic methods utilizing a redox reaction have been applied widely to the measurement of various glycated proteins including glycated Hb, and attempts have been made to put these enzymatic methods into practical use. Specifically, the measurement is carried out in the following manner.

First, blood cells are hemolyzed to prepare a sample. To the thus-obtained hemolyzed sample, a protease is added so that a degradation product of glycated Hb is generated. Then, a fructosyl amino acid oxidase (hereinafter referred to as "FAOD") further is added to the degradation product so that the FAOD acts on a glycation site of the glycated Hb to cause a redox reaction, thereby generating hydrogen peroxide. The amount of the hydrogen peroxide corresponds to the amount of the glycated protein. Then, a peroxidase (hereinafter referred to as "POD") and a substrate that develops color by oxidation are added to the reaction solution so that the substrate develops color through the enzyme reaction. The amount of the hydrogen peroxide can be determined by measuring the color developed. As a result, the amount of the glycated protein in the blood cells can be determined.

However, as described above, such an enzymatic method also has a problem in that the measured value becomes greater than the true value owing to a glycation product as a non-analyte contained in the sample. Therefore, in order to solve this problem, the applicant of the present invention proposed the following enzymatic methods (e.g., Patent Document 2).

That is, the applicant of the present invention proposed, as a first method, a method of measuring glycated Hb as an analyte by adding a FAOD (a degradation FAOD) exhibiting a low reactivity to the glycated Hb to a sample beforehand to treat a glycation product as a non-analyte and then treating a degradation product of the glycated Hb obtained through a protease treatment with a FAOD (a measurement FAOD) exhibiting a high reactivity to the glycated Hb.

The applicant of the present invention also proposed, as a second method, a method of measuring glycated Hb as an analyte by pretreating a sample with a small amount of a FAOD (a degradation FAOD) exhibiting a high reactivity to the glycated Hb beforehand, then treating the sample with a protease, and adding the same FAOD (a measurement FAOD) again to the sample. In this second method, the reason why the amount of the degradation FAOD to be added is small, more specifically, the reason why the ratio of the pretreatment FAOD to the measurement FAOD is small, is that this allows the glycated Hb to be prevented from reacting with the FAOD during the pretreatment in terms of the kinetics. Moreover, in the second method, the protease is added not only to degrade the glycated Hb but also to deactivate the degradation FAOD added first. This is because, if the degradation FAOD added first remains, the degradation product of the glycated Hb generated by adding the protease reacts with the remaining FAOD.

[Patent Document 1] JP 2000-180439 A
[Patent Document 2] WO 03/033729

DISCLOSURE OF INVENTION

Problem to be Solved by the Invention

According to the first conventional enzymatic method, the pretreatment FAOD pretreats a non-analyte beforehand. However, since the measurement FAOD used for causing the main reaction has a catalytic function different from that of the pretreatment FAOD, a non-analyte on which this measurement FAOD can act is not treated completely by this pretreatment. Thus, although the first conventional enzymatic method can improve the measurement accuracy, still further improvement in the accuracy has been demanded. Moreover, according to the first enzymatic method, three steps of reactions using at least three types of reagents, namely, (1) the pretreatment FAOD, (2) the protease, and (3) the measurement FAOD (+POD), respectively, have to be performed, so that it takes a long time to complete the measurement and also it requires laborious procedures of preparing the reagents.

On the other hand, according to the second conventional enzymatic method, the amount of the pretreatment FAOD to be added has to be small and deactivating the pretreatment FAOD almost completely before adding the measurement FAOD is important, as described above. However, when the amount of the pretreatment FAOD is small, a treating period sufficient for the consumption of the non-analyte needs to be secured. Thus, in order to allow the non-analyte to be consumed completely, the treating period has to be long, which prolongs the entire measurement period. Furthermore, the fact that none of the treatment with the pretreatment FAOD, the treatment with the protease, and the treatment with the measurement FAOD can be performed simultaneously with another also affects the measurement period.

Therefore, with the foregoing in mind, it is an object of the present invention to provide a method of measuring a glycated amine, which enables highly reliable measurement of the glycated amine easily and conveniently.

Means for Solving Problem

In order to achieve the above object, a method of measuring a glycated amine according to the present invention includes the steps of: adding a protease to a sample to degrade a glycated amine as an analyte contained in the sample with the protease; adding a FAOD to the sample so that the FAOD acts on the degradation product of the glycated amine, thereby causing a redox reaction; measuring the redox reaction; and determining an amount of the glycated amine based on a result of the measurement of the redox reaction. The method further includes, prior to the degradation step of adding the protease, a step of adding the FAOD to the sample to cause the FAOD to act on a non-analyte glycated amine that is present in the sample and different from the glycated amine as the analyte in order to remove an influence of the non-analyte glycated amine, and the redox reaction after the degradation step is caused by the FAOD added prior to the degradation step. Note here that, in the present invention, a glycated amine to be measured also is referred to as an "analyte glycated amine", a glycated amine not to be measured also is referred to as a "non-analyte glycated amine", a reaction of a non-analyte glycated amine with a FAOD also is referred to as a "pretreatment reaction", and a reaction of an analyte glycated amine with a FAOD also is referred to as a "main reaction".

It should be noted that "FAOD" merely is a generic name and the substrate specificity thereof varies depending on its type. Thus, a FAOD can act not only on a glycated amino acid but also on a glycated peptide or a glycated protein. It also should be noted that, although the glycated amine encompasses a glycated protein, a glycated peptide, a glycated amino acid, and the like, an "analyte glycated amine" as used in the present invention refers to a glycated protein or a glycated peptide.

Effects of the Invention

The inventor of the present invention conducted in-depth research concerning a method of measuring glycated amines including glycated Hb. As a result, the inventor arrived at a method of measuring a glycated amine according to the present invention, in which a non-analyte glycated amine is treated by adding a FAOD to a sample beforehand and protease then is added to degrade an analyte glycated amine so that the already added FAOD acts on the degradation product of the analyte glycated amine obtained by the degradation with the protease. In this method, the non-analyte is treated by adding the FAOD to the sample beforehand. Thus, the non-analyte that can react with the FAOD already is consumed when causing the degradation reaction with the protease and the main reaction. Therefore, it is possible to prevent a false positive result and an increase in the measured value (the tendency that the measured value becomes greater than the true value) due to the non-analyte, so that particularly excellent measurement accuracy can be attained. Moreover, according to the present invention, as long as the non-analyte glycated amine is treated with the FAOD beforehand, the degradation of the analyte with the protease, the redox reaction, and the like then may be performed sequentially or simultaneously as will be described later. Therefore, the number of reaction steps in the measurement can be reduced to as small as two, which allows the measurement to be carried out simply. It is to be noted that conventional enzymatic methods, which have been applied widely not only to clinical tests but also to food analyses etc., are carried out basically by treating a sample with a protease and then adding an enzyme for causing a main reaction. Therefore, it was first discovered by the inventor of the present invention that a FAOD as an enzyme for causing a main reaction could be added before adding a protease. Therefore, by applying the measurement method of the present invention to, for example, the measurement of glycated Hb, the reliability of the glycated Hb as an indicator in the diagnosis and the like of diabetes increases. As a result, the method of the present invention becomes useful in the field of clinical medicine and the like.

DESCRIPTION OF THE INVENTION

As described above, the measurement method of the present invention includes the steps of: adding a protease to a sample to degrade a glycated amine as an analyte contained in the sample with the protease; adding a FAOD to the sample so that the FAOD acts on the degradation product of the glycated amine, thereby causing a redox reaction; measuring the redox reaction; and determining an amount of the glycated amine based on a result of the measurement of the redox reaction. The method further includes, prior to the degradation step of adding the protease, a step (a pretreatment step) of adding the FAOD to the sample to cause the FAOD to act on a non-analyte glycated amine that is present in the sample and different from the glycated amine as the analyte in order to remove an influence of the non-analyte glycated amine, and the redox reaction after the degradation step is caused by the FAOD added prior to the degradation step. In other words, the FAOD added to the sample to treat the non-analyte glycated amine prior to the degradation step further can cause the redox reaction after the degradation step.

The analyte is not particularly limited and can be measured by the method of the present invention, as long as it is a glycated amine that can utilize the above-described redox reaction. Specific examples of the analyte glycated amine include glycated proteins such as glycated Hb and glycated albumins and glycated peptides. Among these, the measurement method of the present invention particularly is useful for the measurement of glycated amines present in blood cells, in particular, glycated Hb.

In the present invention, it is preferable that the step of causing the redox reaction is, for example, a step of causing the FAOD to act on the degradation product of the glycated amine to generate hydrogen peroxide and that the step of measuring the redox reaction includes a step of adding an oxidase (e.g., a POD) and a substrate that develops color by oxidation to the sample so that a reaction between the generated hydrogen peroxide and the substrate is caused by the oxidase. The substrate develops color through this reaction, and the redox reaction can be measured by measuring the amount of color developed.

In the present invention, it is preferable that the degradation step, the step of causing the redox reaction, and the step of measuring the redox reaction are performed at the same time. This reduces the number of steps required for the measurement, so that the operation of the measurement can be performed quickly and simply. Specifically, these three steps can be performed at the same time by, for example, (1) adding the protease, the oxidase, and the substrate that develops color by oxidation to the sample at the same time after the pretreatment step, (2) adding the oxidase to the sample together with the FAOD prior to the degradation step and further adding the protease and the substrate that develops color by oxidation to the sample at the same time, or (3) adding the substrate that develops color by oxidation to the sample together with the FAOD prior to the degradation step and further adding the protease and the oxidase to the sample at the same time.

In the measurement method according to the present invention, FAODs catalyzing a reaction represented by Formula (1) below preferably are used. Examples of such FAODs include a FAOD specific for a glycated amine having a glycated α-amino group (hereinafter referred to as a "FAOD-α"), a FAOD specific for a glycated amine having a glycated amino group in a side chain of an amino acid residue (hereinafter referred to as a "FAOD-S"), and a FAOD specific for both a glycated amine having a glycated α-amino group and a glycated amine having a glycated amino group in a side chain of an amino acid residue (hereinafter referred to as a "FAOD-αS").

$$R^1\text{—CO—CH}_2\text{—NH—}R^2 + H_2O + O_2 \rightarrow R^1\text{—CO—CHO} + NH_2\text{—}R^2 + H_2O_2 \quad (1)$$

In Formula (1), $R^1$ denotes a hydroxyl group or a residue derived from the sugar before glycation (i.e., sugar residue). The sugar residue ($R^1$) is an aldose residue when the sugar before glycation is aldose, and is a ketose residue when the sugar before glycation is ketose. For example, when the sugar before glycation is glucose, it takes a fructose structure after glycation by an Amadori rearrangement. In this case, the sugar residue ($R^1$) becomes a glucose residue (an aldose residue). This sugar residue ($R^1$) can be represented, for example, by —[CH(OH)]$_n$—CH$_2$OH where n is an integer of 0 to 6.

In Formula (1), $R^2$ is not particularly limited. However, when the glycated amine is a glycated amino acid or a glycated peptide (including a glycated protein), there is a difference between the case where an α-amino group is glycated and the case where an amino group other than the α-amino group (i.e., an amino group in a side chain of an amino acid residue) is glycated.

In Formula (1), when an α-amino group is glycated, $R^2$ is an amino acid residue or a peptide residue represented by Formula (2) below. The above-described FAOD-α and FAOD-αS specifically catalyze the reaction represented by Formula (1) in this case.

—CHR$^3$—CO—R$^4$ (2)

In Formula (2), $R^3$ denotes an amino-acid side chain group. $R^4$ denotes a hydroxyl group, an amino acid residue, or a peptide residue, and can be represented by, for example, Formula (3) below. In Formula (3), n is an integer of 0 or more, and $R^3$ denotes an amino-acid side chain group as in the above. When n is an integer of more than 1, the amino-acid side chain groups may be either the same or different.

—(NH—CR$^3$H—CO)$_n$—OH (3)

In Formula (1), when an amino group other than the α-amino group is glycated (i.e., an amino-acid side chain group is glycated), $R^2$ can be represented by Formula (4) below. The above-described FAOD-S and FAOD-αS specifically catalyze the reaction represented by Formula (1) in this case.

—R$^5$—CH(NH—R$^6$)—CO—R$^7$ (4)

In Formula (4), $R^5$ denotes a portion other than the glycated amino group in the amino-acid side chain group. For example, when the glycated amino acid is lysine, $R^5$ is as follows.

—CH$_2$—CH$_2$—CH$_2$—CH$_2$—

For another example, when the glycated amino acid is arginine, $R^5$ is as follows.

—CH$_2$—CH$_2$—CH$_2$NH—CH(NH$_2$)—

In Formula (4), $R^6$ denotes hydrogen, an amino acid residue, or a peptide residue, and can be represented by, for example, Formula (5) below. In Formula (5), n denotes an integer of 0 or more, and $R^3$ denotes an amino-acid side chain group as in the above. When n is an integer of more than 1, the amino-acid side chain groups may be either the same or different.

—(CO—CR$^3$H—NH)$_n$—H (5)

In Formula (4), $R^7$ denotes a hydroxyl group, an amino acid residue, or a peptide residue, and can be represented by, for example, Formula (6) below. In Formula (6), n is an integer of 0 or more, and $R^3$ denotes an amino-acid side chain group as in the above. When n is an integer of more than 1, the amino-acid side chain groups may be either the same or different.

—(NH—CHR$^3$—CO)$_n$—OH (6)

Examples of the FAOD-α specific for a glycated α-amino group include a commercially available product named Fructosyl-Amino Acid Oxidase (FAOX-TE) (manufactured by Kikkoman Corporation) and FAODs derived from the genus *Penicillium* (JP 8(1996)-336386 A). Examples of the FAOD-S specific for a glycated side chain of an amino acid residue include FAODs derived from the genus *Fusarium* ("Conversion of Substrate Specificity of Amino Acid Oxidase Derived from *Fusarium oxysporum*" by Maki FUJIWARA et al., Annual Meeting 2000, The Society for Biotechnology, Japan). Furthermore, examples of FAOD-αS specific for both a glycated α-amino group and a glycated side chain group include a commercially available product named FOD (manufactured by Asahi Chemical Industry Co., Ltd.), FAODs derived from the genus *Gibberella* (JP 8(1996)-154672 A), FAODs derived from the genus *Fusarium* (JP 7(1995)-289253 A), and FAODs derived from the genus *Aspergillus* (WO 99/20039).

The FAOD to be used can be decided as appropriate depending on the type of the analyte glycated amine. When the analyte is glycated Hb as described above, it is preferable to use a FAOD-α specific for a glycated α-amino group because HbA1c (%) can be calculated by measuring the degree of glycation of an α-amino group in the N-terminal valine of the hemoglobin β-chain. In particular, since a product named FAOX-TE as a FAOD-α is specific for a released "vahne" having a glycated α-amino group, it can be used suitably when measuring the degree of glycation by releasing Val from the β-chain N-terminal valine with a N-terminal sequence of "Val-His-Leu . . . " or from the α-chain N-terminal valine with a N-terminal sequence of "Val-Leu-Ser-Pro-Ala-Asp . . . ". The FAOD-α and, in particular, a FAOD obtained from *Fusarium* sp.GL2-1 (FERM BP-8451) by an ordinary method also can be used. Such a FAOD-α is specific for a released Val having a glycated α-amino group, Val-Leu, Val-Leu-Ser, Val-His, Val-His-Leu, and the like, and thus can be used suitably when measuring an amount of glycation by releasing these sequences from the N-terminal of the α-chain or β-chain. When the analyte is an amino acid having a glycated α-amino group (glycated Val), a peptide having a glycated α-amino group (glycated Val-His), an amino acid having a glycated ε-amino group (glycated Lys), a peptide having a glycated ε-amino group (glycated Lys-Thr, glycated Lys-Ser), or the like, it is preferable to use a FAOD-AS specific for both glycated Lys and glycated Val.

The type of the protease is not particularly limited, and at least one protease selected from the group consisting of metalloproteinase, bromelain, papain, trypsin, proteinase K, subtilisin, and aminopeptidase can be used. However, the protease preferably is selected depending on the type of an analyte glycated amine, and it is particularly preferable to use a protease that can degrade the analyte glycated amine selectively or a protease that specifically can release a degradation product on which a FAOD can act easily. This is because, by using the protease that can degrade the analyte glycated amine selectively, it is possible to improve the measurement accuracy further because, for example, even when a glycated amine (in particular, a glycated protein, a glycated peptide) other than the analyte glycated amine is present in the sample, such a non-analyte glycated amine hardly is degraded and thus there is no fear that a degradation product on which the FAOD can act easily might be generated. More specifically, when the analyte is glycated Hb as described above, it is preferable to use a protease that degrades the glycated Hb selectively. Examples of such a protease include metalloproteinase, bromelain, papain, trypsin derived from porcine pancreas, and proteases derived from *Bacillus subtilis*. Among these, metalloproteinase and protease derived from *Bacillus subtilis* are more preferable, and metalloproteinase is particularly preferable.

Furthermore, when a FAOD-α as described above is used, it is preferable to use a protease that specifically can release a degradation product on which the FAOD-α can act easily, e.g., β-chain N-terminal valine or a peptide (e.g., dipeptide, tripeptide, or the like) containing this valine. As such a protease, it is possible to use subtilisin, pronase, an angiotensin converting enzyme, or the like. More specifically, for example, a tripeptide with a sequence of Val-His-Leu can be released by treating glycated Hb with subtilisin, pronase, or the like, and glycated valine (fructosyl valine) further can be released from the tripeptide by treating the tripeptide with an angiotensin converting enzyme specific for His-Leu.

Furthermore, when a FAOD-α derived from the genus *Fusarium* (e.g., *Fusarium* sp.GL2-1 (FERM BP-8451)) is used, it is preferable to use, for example, a protease that specifically can release α-chain N-terminal valine or a peptide (e.g., dipeptide, tripeptide, or the like) containing this valine. For example, endoproteinase ASP-N or the like can be used. More specifically, for example, a peptide with a sequence of Val-Leu-Ser-Pro-Ala-Asp can be released by treating glycated Hb with the endoproteinase ASP-N, and glycated Val-Leu further can be released from the peptide by treating the peptide with carboxypeptidase Y Furthermore, when the analyte is a glycated albumin, it is possible to use proteinase K, subtilisin, ficin, elastase, thermolysin, or the like, for example, and any type of albumin (e.g., HSA, BSA, and the like) can be measured without any limitation, regardless of where they are derived.

In the present invention, the sample used for measurement is not particularly limited. For example, the measurement method according to the present invention can be applied to biological samples such as whole blood, plasma, serum, blood cells, urine, and spinal fluid, drinks such as juices, and foods such as soy sauce and Worcestershire sauce. Among these, the measurement method according to the present invention particularly is useful for the blood samples such as whole blood, plasma, serum, and blood cells as described above and the biological samples other than those, for example. For example, when a glycated amine as a component in blood cells is to be measured, whole blood itself may be hemolyzed to prepare a sample, or erythrocytes may be separated from whole blood and hemolyzed to prepare a sample. In many cases, fluid or the like administered to a patient via an intravenous drip or the like contains a saccharide such as glucose and any of various amino acids, for example. Thus, there is a possibility that a glycated amine may be formed from such components, resulting in a temporary increase in glycated amino acid in the blood or the like of the patient. Therefore, the measurement method of the present invention is very useful for a blood sample or the like collected from the patient after being put on an intravenous drip, for example In the present invention, the redox reaction preferably is measured by measuring an amount of hydrogen peroxide derived from the analyte glycated amine, generated through the redox reaction of the FAOD. The amount of the hydrogen peroxide can be determined by, for example, causing the hydrogen peroxide derived from the analyte glycated amine to be reduced and a substrate that develops color by oxidation (a color-developing substrate) to be oxidized at the same time by the POD and then measuring the degree of the color developed by the substrate.

The order of adding the POD is not particularly limited. For example, the POD may be added before or after adding the protease, or alternatively, the POD may be added simultaneously with the protease. Similarly, there is no limitation regarding the order of adding the color-developing substrate. A specific example will be given later.

Next, the measurement method of the present invention will be described with reference to an example where glycated Hb in blood cells is measured using a whole blood sample containing a non-analyte. In this embodiment, unless otherwise stated, a "glycated amino acid" refers to a glycated amino acid as a non-analyte contained in a sample and does not include a glycated amino acid as a degradation product of a glycated protein as an analyte obtained through a treatment with a protease.

First, whole blood is hemolyzed to prepare a hemolyzed sample. The method of causing the hemolysis is not particularly limited, and can be, for example, a method using a surfactant, a method using ultrasonic waves, a method utilizing a difference in osmotic pressure, and a method using a freeze-thawing technique. Among these, the method using a surfactant is preferable because of its simplicity in operation, etc.

As the surfactant, for example, non-ionic surfactants such as polyoxyethylene-p-t-octylphenyl ether (e.g. Triton series surfactants), polyoxyethylene sorbitan alkyl ester (e.g. Tween series surfactants), polyoxyethylene alkyl ether (e.g. Brij series surfactants), and the like can be used. Specific examples are products named Triton X-100, Tween-20, Brij 35, and the like. The conditions for the treatment with the surfactant usually may be as follows: when the concentration of blood cells in the solution to be treated is in the range from 1 to 10 vol %, the surfactant is added to the solution so that its concentration in the solution is in the range from 0.1 to 1 wt %, and the solution then is stirred at room temperature for about 5 seconds to 1 minute.

Furthermore, when utilizing the difference in osmotic pressure, to the whole blood is added 2 to 100 times its volume of purified water to cause hemolysis, for example.

Next, a FAOD is added to the hemolyzed sample. By adding the FAOD, a non-analyte glycated amine that is present in the hemolyzed sample and can serve as a substrate of the FAOD is degraded (the pretreatment step). More specifically, through the reaction of Formula (1) catalyzed by the FAOD, the glycation site of the non-analyte glycated amine is degraded while generating hydrogen peroxide. Since the non-analyte glycated amine that can react with the FAOD already has been degraded at this stage as described above, there is no fear that the FAOD added in this step might react with the non-analyte when glycated Hb is degraded with a protease in the subsequent step. Thus, it is possible to cause only the degradation product of the glycated Hb to react with the FAOD. Note here that this step can be performed simultaneously with the treatment for causing hemolysis (hereinafter referred to as "hemolysis treatment").

It is to be noted here that the non-analyte-derived hydrogen peroxide generated in this step disappears quickly immediately after its generation due to glutathione peroxidase or catalase present in the blood cells. Accordingly, there is no chance that the hydrogen peroxide generated at this stage might affect the measurement (the POD reaction) of hydrogen peroxide derived from glycated Hb, which will be described later. The fact that the hydrogen peroxide is consumed immediately after its generation is apparent from the ratio between Hb and the non-analyte in the reaction solution and from the chemical kinetics, for example. Also, the fact that the hydrogen peroxide does not affect the POD reaction is apparent from the results of examples that will be described later.

Thus, when the analyte glycated amine is any of blood cell components including glycated Hb, the hydrogen peroxide generated by the degradation of the non-analyte glycated amine is degraded quickly by catalase or the like that are present originally in the blood cells, which eliminates the necessity of adding catalase or the like separately, so that the operation of the measurement can be carried out still more simply. When the sample does not contain blood cells (e.g., a serum sample, urine, or the like), in other words, when the sample does not contain catalase present in the blood cells, catalase may be added separately so as to remove the hydrogen peroxide derived from the non-analyte glycated amine. When the hydrogen peroxide is removed by the catalase, it is preferable to add excess amounts of POD and color-developing substrate when measuring the above-described redox reaction in order to prevent hydrogen peroxide formed by the FAOD treatment to be performed later from also being removed. Preferably, the POD and the color-developing substrate are added, for example, either before adding the FAOD or simultaneously with the FAOD. In this case, with respect to the amount (U) of the catalase added, the POD preferably is added so that its activity (U) becomes 5 to 100 times, for example.

The method of treating the hydrogen peroxide derived from the non-analyte glycated amine is not limited to the above method but the following methods also may be used. For example, before adding the protease, electron donors may be present with the FAOD and the POD. According to this method, before adding the protease, the hydrogen peroxide derived from the non-analyte glycated amine is dehydrogenated through the POD reaction so that electrons generated through this reaction are donated to the electron donors. Accordingly, when the protease is added later, the hydrogen peroxide has already been consumed, so that it does not affect the measurement of the analyte glycated amine. Furthermore, a FAOD, a POD, and a color developing agent that develops color by oxidation may be added before adding a protease so as to measure the amount of color developed at this time beforehand, and the thus-obtained amount of the color developed may be used to correct the measurement result.

The amount of the FAOD to be added to the hemolyzed sample may be such that the non-analyte and a Hb degradation product that will be described later can be treated with the FAOD sufficiently. For example, the amount of the FAOD can be determined as appropriate depending on the Hb concentration in the hemolyzed sample or the like, but it is preferable to add an excess amount of FAOD in order to remove the non-analyte rapidly. Specifically, when the concentration of blood cells in the reaction solution is 0.3 vol %, the FAOD is added so that, for example, its concentration is in the range from 0.1 to 30 U/l, preferably 2 to 10 U/l, and more preferably 3 to 6 U/l. Furthermore, when the concentration of whole blood in the reaction solution is 0.3 vol %, the FAOD is added so that its concentration is in the range from 0.1 to 45 U/l, preferably 2 to 15 U/l, and more preferably 3 to 9 U/l.

The conditions for this FAOD treatment are not particularly limited, but may be as follows: a reaction temperature is in the range from, for example, 2° C. to 60° C., preferably 4° C. to 40° C.; a reaction period is in the range from, for example, 1 to 30 minutes, preferably 3 to 5 minutes; and a pH is in the range from, for example, 6 to 9. This treatment usually is carried out in a buffer. The type of the buffer is not particularly limited, and for example, Tris-HCl buffer, phosphate buffer, EPPS buffer, PIPES buffer, and the like can be used.

It is to be noted here that, although the step of causing hemolysis and the step of adding the FAOD may be performed separately, it is preferable to perform these steps at the same time from the aspect of reducing the time required for the measurement and simplifying the measurement process. In particular, considering the case where the measurement method of the present invention is carried out with the use of a reagent kit, the hemolysis and the FAOD treatment of the non-analyte glycated amine preferably are performed at the same time, because this reduces the number of reagents to be used.

Subsequently, to the reaction solution to which the FAOD has been added, a protease, a POD and a substrate that develops color by oxidation (a color-developing substrate) further are added. By adding the protease, the glycated Hb is degraded so that the FAOD that has been added can act thereon easily. Thus, the reaction represented by Formula (1) is caused between the degradation product of the glycated Hb and the FAOD, so that hydrogen peroxide derived from the glycated Hb is generated. That is, by adding the protease, the redox reaction is caused automatically by the FAOD that has been added already. The hydrogen peroxide thus generated is reduced by the POD immediately, and the color-developing substrate that also is present in the reaction solution is oxidized to develop color. The color developed can be measured by, for example, measuring the absorbance of the reaction solution with a spectrophotometer or the like, and the amount of the hydrogen peroxide can be determined based on the result of the measurement of the absorbance. Then, for example, the amount of the glycated Hb (the amount of glycation) in the sample can be determined using the concentration of the hydrogen peroxide and a calibration curve or the like.

This treatment usually is carried out in a buffer exemplified above, and the conditions for the treatment are determined as appropriate depending on the type of the protease used, the type and the concentration of the glycated protein as the analyte, etc.

The concentration of the protease in the reaction solution is, for example, in the range from 10 KU/l to 300 MU/l, preferably from 1 MU/U to 60 MU/l, and more preferably 5 MU/l to 30 MU/l when the concentration of blood cells is 0.3 vol %, and is in the range from 10 KU/l to 150 MU/l, preferably from 1 MU/l to 30 MU/l, and more preferably 5 MU/l to 15 MU/l when the concentration of whole blood is 0.3 vol %.

Preferably, an excess amount of the POD is present in the reaction solution, for example. This is because, when an excess amount of the POD is present in the reaction solution, the hydrogen peroxide can react with the POD quickly immediately after its generation, so that the influence of catalase present in the sample can be suppressed sufficiently, for example. Specifically, when the concentration of blood cells in the reaction solution is 0.3 vol %, the concentration of the POD is, for example, in the range from 0.01 KU/l to 4 MU/l, preferably from 0.1 KU/l to 200 KU/l, and more preferably 5 KU/l to 100 KU/l, and when the concentration of whole blood in the reaction solution is 0.3 vol %, the concentration of the POD is, for example, in the range from 0.01 KU/l to 2 MU/l, preferably from 0.1 KU/l to 100 KU/l, and more preferably 5 KU/l to 50 KU/l. The concentration of the color-developing substrate the reaction solution is, for example, in the range from 0.01 to 300 µmol/l, preferably from 1 to 100 µmol/l, and more preferably 5 to 30 µmol/l when the concentration of blood cells is 0.3 vol %.

The conditions for this treatment are not particularly limited, but may be as follows: a reaction temperature is in the range from, for example, 2° C. to 60° C., preferably 4° C. to 40° C.; a reaction period is in the range from, for example, 1 to 30 minutes, preferably 3 to 10 minutes; and a pH is in the range from, for example, 6 to 9.

As the color-developing substrate, N-(carboxymethylaminocarbonyl)-4,4'-bis(dimethylamino)diphenylamine sodium salt, orthophenylenediamine (OPD), a substrate in which a Trinder's reagent and 4-aminoantipyrine are combined, and the like can be used, for example. Examples of the Trinder's reagent include phenols, phenol derivatives, aniline derivatives, naphthols, naphthol derivatives, naphthylamine, and naphthylamine derivatives. Furthermore, in place of the aminoantipyrine, it is possible to use an aminoantipyrine derivative, vanillin diamine sulfonic acid, methylbenzothiazolinone hydrazone (MBTH), sulfonated methylbenzothiazolinone hydrazone (SMBTH), or the like. Among these color-developing substrates, N-(carboxymethylaminocarbonyl)-4,4'-bis(dimethylamino)diphenylamine sodium salt is particularly preferable.

In the present invention, the protease treatment and the POD treatment can be performed separately by adding the POD and the color-developing substrate to the sample after adding the protease. However, for the following reasons, it is preferable to perform both the treatments at the same time. The first reason is that, when the protease is added together with the POD and the color-developing substrate, the hydrogen peroxide generated reacts with the POD immediately, so that there is no fear that the hydrogen peroxide might be consumed by catalase as described above. The second reason is that, when both the treatments are performed as a single step, the measurement can be carried out still more simply and quickly. Finally, the third reason is that, considering the case where the measurement is carried out using a reagent kit, the reduction in the number of steps results in the reduction in the number of reagents to be used, so that the reagent kit can be produced at low cost. In particular, it is to be noted here that the second conventional enzymatic method generally requires three or more steps including at least a treatment with a degradation FAOD, a treatment with a protease, and a treatment with a measurement FAOD and that the first conventional enzymatic method needs to employ an at least three-reagent system because a protease and a measurement FAOD need to be prepared as separate reagents from the aspect of the stability of the measurement FAOD. However, according to the present invention, the number of reaction steps may be very small, more specifically, two steps in total with the non-analyte being removed by a single step (which may include the hemolysis treatment) and the protease treatment and the POD treatment being performed as a single step. Therefore, according to the present invention, it is possible to realize the measurement with a two-reagent system using a reagent containing a FAOD (and optionally containing a hemolysis reagent) and a reagent containing a protease, a POD, and a color-developing substrate. The realization of the measurement using a two-reagent system is extremely advantageous in terms of cost and ease of operation.

Furthermore, the protease treatment and the POD treatment can be performed at the same time by, for example, adding the protease, the POD, and the color-developing substrate to the sample at the same time after causing the FAOD to act on the non-analyte glycated amine as described above. This also can be achieved by adding the POD to the sample together with the FAOD prior to the degradation step and further adding the protease and the color-developing substrate to the sample at the same time. Furthermore, this also can be achieved by adding the color-developing substrate to the sample together with the FAOD prior to the degradation step and further adding the protease and the POD to the sample at the same time. In such cases, a hemolysis treatment can be carried out by further adding a hemolysis reagent together with the FAOD.

The amount of the hydrogen peroxide can be measured not only by the above-described enzymatic method using the POD etc. but also by an electrical method, for example.

Moreover, in the present invention, in order to improve the measurement accuracy further, various additives can be added prior to the degradation step using the protease. Examples of the additive include tetrazolium compounds. By adding a tetrazolium compound, various advantageous effects described below can be obtained, for example. Usually, reducing substances such as ascorbic acid are present in a blood sample or the like, and a problem may occur in that a substrate that has developed color by oxidation is reduced by these reducing substances so that the color developed disappears. However, such a problem can be avoided by adding a tetrazolium compound, thereby allowing the measurement accuracy to be improved further. Moreover, adding a tetrazolium compound can produce another advantageous effect that the degradation of the analyte glycated amine is accelerated to allow the FAOD to act on the degradation product efficiently.

The type of the tetrazolium compound is not particularly limited, and 2-(4-iodophenyl)-3-(2,4-dinitrophenyl)-5-(2,4-disulfophenyl)-2H-tetrazolium or a salt thereof (e.g., monosodium salt) can be used, for example.

It is to be noted here that not only the tetrazolium compound but also a sulfonic acid compound, a nitro compound, and the like disclosed in WO 03/107011 can be used for a similar purpose. Specific examples of the sulfonic acid compound and the nitro compound include: sodium lauryl sulfate (SLS), sodium dodecylbenzenesulfonate (SDBS), lithium lauryl sulfate (LiLS), 4-aminoazobenzene-4'-sulfonic acid sodium salt (ABSA), 4-amino-4'-nitrostilbene-2,2'-disulfonic acid disodium salt (ANDS), 4,4'-diazidostilbene-2,2'-disulfonic acid disodium salt (DADS), N-cyclohexyl-2-aminoethane sulfonic acid, N-cyclohexyl-3-aminopropane sulfonic acid, N-cyclohexyl-2-hydroxy-3-aminopropane sulfonic acid, piperazine-1,4-bis(2-ethane sulfonic acid), and bathophenanthroline sulfonic acid; and 2,4-dinitrophenol (2,4-DNP), 2,5-dinitrophenyl, 2,6-dinitrophenyl, 4,6-dinitro-2-methyl phenol, 2-amino-4-nitrophenol, 2-amino-5-nitrophenol, 2-amino-4-nitrophenol, p-nitrophenol (p-NP), 2,4-dinitroaniline (2,4-DNA), p-nitroaniline (p-NA), sodium nitrite ($NaNO_2$), potassium nitrite ($KNO_2$), 4-amino-4'-nitrostilbene-2,2'-disulfonic acid disodium salt (ANPS), and nitrobenzene.

Moreover, in order to further enhance the above-described effects of the tetrazolium compound, it is preferable that the tetrazolium compound is added to the sample together with a surfactant, for example. The surfactant to be used is not particularly limited. Examples of the surfactant include: nonionic surfactants typified by Triton X-100 and TWEEN 20; anionic surfactants typified by sodium dodecyl sulfate, lithium dodecyl sulfate, and CHAPS; and cationic surfactants typified by benzalkonium chloride. Other than these, urea or the like can be used as an additive.

In general, a ratio of a glycated amine (in particular, a glycated protein) can be determined by measuring the amount of protein and the amount of glycated protein and then calculating the ratio of the glycated protein from these measured values. In the measurement method according to the present invention, when the analyte glycated amine is glycated Hb, Hb can be measured by a conventionally known method. However, Hb also can be measured by, for example, adding a tetrazolium compound, sodium dodecyl sulfate, lithium dodecyl sulfate, sodium azide, or the like to the sample so as to stabilize the Hb by denaturing it and then measuring the absorbance of the sample (see WO 02/27330, for example). Furthermore, when the analyte glycated amine is glycated albumin, the amount of albumin can be measured by using a known substance such as o-cresol or bromcresol green.

Next, a measuring kit according to the present invention is a two-reagent system kit including a first reagent and a second reagent for use in the above-described measurement method of the present invention. The first reagent contains at least a FAOD, and the second reagent contains at least a protease. Moreover, one of a POD and a substrate that develops color by oxidation is contained in the first reagent whereas the other is contained in the second reagent, or alternatively, both the POD and the substrate are contained in the second reagent.

Specific examples (A to C) of the combination of the first reagent and the second reagent in the measuring kit of the present invention are shown below.

| (A) | First reagent: | FAOD |
|---|---|---|
|  | Second reagent: | protease + POD + color-developing substrate |
| (B) | First reagent: | FAOD + POD |
|  | Second reagent: | protease + color-developing substrate |
| (C) | First reagent: | FAOD + color-developing substrate |
|  | Second reagent: | protease + POD |

Moreover, in the reagent kit of the present invention, the first reagent may further contain, for example, additives such as a tetrazolium compound, a sulfonic acid compound, a nitro compound, and a surfactant that can be added to the sample prior to the degradation step, in order to improve the measurement accuracy further. Furthermore, when blood cells are to be hemolyzed, the first reagent further may contain a hemolysis reagent. The contents of the respective components in each of the reagents are not particularly limited, and can be set as appropriate so that, when these components are added to the reaction system, the concentrations thereof in the reaction solution would be fall within the above-described ranges.

The measurement method of the present invention can be carried out using such a reagent kit of the present invention by, for example, adding the first reagent and then adding the second reagent to a sample. The treatment conditions (e.g., a temperature and a treating period) after the first reagent has been added and the treatment conditions after the second reagent has been added are as described above.

Example 1

(I) Various glycated amino acids were added to blood cell samples as non-analyte glycated amines, and the measurement of HbA1c in blood cells was performed with respect to each sample.

Blood Cell Sample

Blood collected from a healthy subject was centrifuged (3000 G, 10 min). To the collected blood cells, a glycated amino acid aqueous solution described later and water were added. Thus, whole blood samples with a hematocrit of 60% were prepared. Note here that the concentrations of the glycated amino acid aqueous solution in the whole blood samples were set to 0 vol %, 1 vol %, and 3 vol %, respectively. The glycated amino acid aqueous solution was a solution containing sixteen types of glycated amino acids (fructosyl isoleucine, fructosyl leucine, fructosyl lysine, fructosyl methionine, fructosyl phenylalanine, fructosyl threonine, fructosyl tryptophan, fructosyl valine, fructosyl tyrosine, fructosyl arginine, fructosyl histidine, fructosyl alanine, fructosyl aspartic acid, fructosyl proline, fructosyl serine, and fructosyl glycine), and the concentration of each glycated amino acid was about 0.02 to 0.4 w/v %.

Example 1

The following operations were carried out using an autoanalyzer (product name JCA-BM 8, Japan Electron Optics Laboratory Co. Ltd.). First, 15 μl of purified water was added to 0.58 μl of the blood cell sample. It is to be noted here that the purified water was added so as to balance the volume of the sample with that of a sample containing a reagent a (15 μl) according to a comparative example to be described later. Subsequently, 74 μl of the following first reagent was added to the blood cell sample. The mixture was incubated at 37° C. for about 4 minutes, and thereafter, the absorbance of the mixture was measured (first measurement). After a lapse of about 1 minute, 18.5 μl of the following second reagent was added to the mixture, and the mixture was incubated at 37° C. for 3 minutes. Thereafter, the absorbance of this reaction solution was measured (second measurement). In both the first and second measurements, the absorbance was measured at a main wavelength of 700 nm and a sub-wavelength of 570 nm. Then, the absorbance obtained in the first measurement was multiplied by 89.58/108.08 so as to correct the absorbance in view of the difference in volume of the sample in the first and second measurements, and the difference (ΔAbs.) between the value of the absorbance obtained in the second measurement and the corrected value of the absorbance obtained in the first measurement was calculated. Then, taking ΔAbs.

with regard to the blood cell sample containing 0 vol % of the glycated amino acid solution as 100%, the relative value (%) of ΔAbs. with regard to each blood cell sample was calculated. The results are shown in Table 1 below as the measurement results of Example 1. The ΔAbs. will be examined later as the HbA1c concentration of the blood sample.

| First reagent | |
|---|---|
| Boric acid (Nacalai Tesque, Inc.) | 1 mmol/l |
| FAOD derived from the genus *Gibberella* (ARKRAY, Inc.) | 5 KU/l |
| Tetrazolium compound (WST-3, Dojindo Laboratories) | 1.7 mmol/l |
| NaN$_3$ (Nacalai Tesque, Inc.) | 0.66 mmol/l |
| Polyoxyethylene lauryl ether (Nikko Chemicals Co. Ltd.) | 1 g/l |

| Second reagent | |
|---|---|
| Tris-HCl buffer | 300 mmol/l |
| POD (Toyobo Co., Ltd.) | 67 KU/l |
| Color-developing substrate (DA-64, Wako Pure Chemical Industries, Ltd.) | 71.3 μmol/l |
| CaCl$_2$ (Nacalai Tesque, Inc.) | 12.5 mmol/l |
| NaCl (Nacalai Tesque, Inc.) | 200 mmol/l |
| Metalloproteinase | 10 MU/l |

Comparative Example 1

This comparative example is directed to a conventional measurement method in which HbA1c as an analyte is measured by degrading a non-analyte glycated amine with a first FAOD and then causing a redox reaction between the HbA1c and a second FAOD that is different from the first FAOD.

The measurement of an absorbance, the determination of ΔAbs., and the calculation of a relative value (%) were carried out in the same manner as in Example 1 except that a reagent a-1 (15 μl) was added instead of the purified water, the following reagent b (74 μl) was added instead of the first reagent, and the following reagent c was added instead of the second reagent. The results are shown in Table 1 below. As the first FAOD contained in the reagent a-1, a product named FAOX-TE (Kikkoman Corporation) was used. As the second FAOD contained in the reagent c, a FAOD derived from the genus *Gibberella* (ARKRAY, Inc.) was used. In Comparative Example 1, the reagent a-1 was used to hemolyze the blood cells and to degrade the non-analyte glycated amine, the reagent b was used to degrade the HbA1c, and the reagent c was used to cause a redox reaction with a degradation product of the HbA1c and to cause a color-developing reaction.

| Reagent a-1 | |
|---|---|
| Polyoxyethylene lauryl ether (Nikko Chemicals Co. Ltd.) | 12 g/l |
| CHES (Dojindo Laboratories) | 80 mmol/l |
| MOPS (Dojindo Laboratories) | 30 mmol/l |
| First FAOD | 0.3 KU/l |

| Reagent b | |
|---|---|
| MES (Dojindo Laboratories) | 1 mmol/l |
| Tetrazolium compound (WST-3, Dojindo Laboratories) | 1.7 mmol/l |
| NaN$_3$ (Nacalai Tesque, Inc.) | 0.66 mmol/l |
| CaCl$_2$ (Nacalai Tesque, Inc.) | 2.5 mmol/l |
| NaCl (Nacalai Tesque, Inc.) | 50 mmol/l |
| Metalloproteinase | 10 MU/l |

| Reagent c | |
|---|---|
| Tris-HCl buffer | 300 mmol/l |
| Second FAOD | 17.4 KU/l |
| POD (Toyobo Co., Ltd.) | 67 KU/l |
| Color-developing substrate (DA-64, Wako Pure Chemical Industries, Ltd.) | 71.3 μmol/l |

Comparative Example 2

This comparative example is directed to a conventional measurement method in which HbA1c as an analyte is measured by degrading a non-analyte glycated amine with a FAOD, deactivating the FAOD with a protease, and then further adding the same FAOD to cause a redox reaction between the HbA1c and this FAOD.

The measurement of an absorbance, the determination of ΔAbs., and the calculation of a relative value (%) were carried out in the same manner as in Comparative Example 1 except that a reagent a-2 used therein corresponded to the reagent a-1 containing a FAOD derived from the genus *Gibberella* (ARKRAY, Inc.) instead of the first FAOD. The results are shown in Table 1 below. In Comparative Example 2, the reagent a-2 and the reagent c contained the same FAOD, and the reagent b was used to degrade the HbA1c and to deactivate the FAOD contained in the reagent a-2.

Comparative Example 3

In Comparative Example 3, the measurement of an absorbance, the determination of ΔAbs., and the calculation of a relative value (%) were carried out in the same manner as in Comparative Example 1 except that a reagent a-3 used therein corresponded to the reagent a-1 with the FAOD being replaced with the same amount of purified water.

TABLE 1

| | Relative value (%) | | | |
|---|---|---|---|---|
| X (vol %) | Ex. 1 | Comp. Ex. 1 | Comp. Ex. 2 | Comp. Ex. 3 |
| 0 | 100 | 100 | 100 | 100 |
| 1 | 103 | 152 | 406 | 1033 |
| 3 | 87 | 294 | 952 | 7513 |

X: the concentration of the glycated amino acid aqueous solution in the blood cell sample (vol %)

As shown in Table 1, in Comparative Example 3 using the reagent a-3 containing no FAOD, since the glycated amino acids added to the sample were not degraded prior to the redox reaction between the HbA1c and the FAOD, the relative value of ΔAbs. increased significantly in keeping with the concentration of the glycated amino acid solution. In particular, the value of ΔAbs. obtained when the sample contained 3 vol % of the glycated amino acid solution was about 75 times that of ΔAbs. obtained when the sample contained 0 vol % of the glycated amino acid solution. Moreover, with regard to Comparative Examples 1 and 2 in which the glycated amino acids added to the sample were treated with the FAOD prior to the redox reaction, the increase in the relative value of ΔAbs. was still significant, although it was not as significant as that in Comparative Example 3. Specifically, in Comparative Example 1, the value of ΔAbs. obtained when the sample contained 3 vol % of the glycated amino acid solution was about 3 times that of ΔAbs. obtained when the sample contained 0 vol % of the glycated amino acid solution, and in Comparative Example 2, the value of ΔAbs. obtained when the sample contained 3 vol % of the glycated amino acid solution was about 9.5 times that of ΔAbs. obtained when the sample contained 0 vol % of the glycated amino acid solution. In contrast, in Example 1, the relative value of ΔAbs. remained substantially constant without changing significantly with an increase in the concentration of the glycated amino acid solution. Even in the case where the sample contained 3 vol % of the glycated amino acid solution, the change in the value of ΔAbs. was only about 10% relative to the value of ΔAbs. obtained when the sample contained 0 vol % of the glycated amino acid solution. These results demonstrate that, according to the example of the present invention, even in the case where a glycated amino acid as a non-analyte is contained in a sample at a high concentration, a highly effective treatment is possible so that an analyte glycated amine can be measured with high accuracy.

(II) Furthermore, the FAOD concentration in the first reagent used in Example 1 was changed, and the measurement of an absorbance and the calculation of a relative value of ΔAbs were carried out in the same manner as in Example 1 (the FAOD concentrations in the first reagent: 3, 5, and 10 KU/l). Also, the FAOD concentration in the reagent a-1 used in Comparative Example 1 and the FAOD concentration in the reagent a-2 used in Comparative Example 2 were changed, and relative values of ΔAbs. were calculated in the same manner (the FAOD concentrations in the reagent a-1 and the reagent a-2: 0.3, 3, and 30 KU/l). These results are shown in Table 2 below. Note here that, in Table 2, the FAOD concentration refers to that in the first reagent with regard to Example 1, that in the reagent a-1 with regard to Comparative Example 1, that in the reagent a-2 with regard to Comparative Example 2, and that in the reagent a-3 with regard to Comparative Example 3.

TABLE 2

|  | FAOD concentration (KU/l) | Relative value (%) X: | | |
|---|---|---|---|---|
|  |  | 0 vol % | 1 vol % | 3 vol % |
| Ex. 1 | 3 | 100 | 103 | 87 |
|  | 5 | 100 | 103 | 87 |
|  | 10 | 100 | 97 | 90 |
| Comp. Ex. 1 | 0.3 | 100 | 313 | 1151 |
|  | 3 | 100 | 152 | 294 |
|  | 30 | 100 | 142 | 225 |
| Comp. Ex. 2 | 0.3 | 100 | 602 | 2589 |
|  | 3 | 100 | 406 | 952 |
|  | 30 | 100 | −219 | −1401 |
| Comp. Ex. 3 | 0 | 100 | 1033 | 7513 |

As shown in Table 2, in contrast to Comparative Example 3 in which no FAOD treatment was performed, in Comparative Example 1, the ability of removing the glycated amino acids added to the sample improved with an increase in the FAOD concentration in the reagent a-1. However, as described above, since the FAOD contained in the reagent a-1 used to remove the glycated amino acids had a catalytic function different from that of the FAOD contained in the reagent c used to cause the redox reaction with the HbA1c as an analyte, the glycated amino acids on which the FAOD in the reagent c could act remained. As a result, it was not possible to suppress further an increase in absorbance. Furthermore, in Comparative Example 2, although the ability of removing the glycated amino acids improved with an increase in the FAOD concentration in the reagent a-2, still further increase in the FAOD concentration caused a large amount of the FAOD to remain without being deactivated with the protease contained in the reagent b. Accordingly, the remaining FAOD reacted with the Hb degradation product before adding the reagent c. Besides, since Comparative Example 2 was directed to the method using a 3-reagent system, the hydrogen peroxide generated by the remaining FAOD was not allowed to react with the POD quickly. As a result, the absorbance decreased contrary to what was proper. In contrast, in Example 1, the absorbance did not change particularly with the concentration of the FAOD. This demonstrates that, according to the method of Example 1, the amount of the FAOD added does not affect the measurement system so that the measurement can be performed with sufficient accuracy.

Example 2

Variants of a two-reagent system reagent kit according to the present invention were examined.

(Sample)

Lyophilized products of glycohemoglobin-controlled blood were dissolved in 1.8 ml of purified water to obtain samples. Note here that the following three types of the lyophilized products were used: the lyophilized product with a low glycohemoglobin concentration (Hb=2.4 g/l, HbA1c %=4.3%), the lyophilized product with an intermediate glycohemoglobin concentration (Hb=3.5 g/l, HbA1c %=9.0%), and the lyophilized product with a high glycohemoglobin concentration (Hb=3.1 g/l, HbA1c %=11.7%).

(Reagent)

First reagents (2-1, 2-2, 2-3) and second reagents (2-1, 2-2, 2-3) shown in Table 3 below were used in combinations as shown in Table 4 below.

TABLE 3

|  | 2-1 | 2-2 | 2-3 |  |
|---|---|---|---|---|
| First reagent | | | | |
| Tris-HCl (pH 7.5) | 10 | 10 | 10 | mmol/l |
| FAOD (ARKRAY, Inc.) | 5 | 5 | 5 | KU/l |
| WST-3 (Dojindo Laboratories) | 1.4 | 1.4 | 1.4 | mmol/l |
| Polyoxyethylene lauryl ether | 1 | 1 | 1 | g/l |
| POD | — | 12 | — | KU/l |
| DA-64 (Wako Pure Chemical Industries, Ltd.) | — | — | 27 | μmol/l |
| Second reagent | | | | |
| Tris-HCl (pH 7.5) | 30 | 30 | 30 | mmol/l |
| protease (ARKRAY, Inc.) | 30 | 30 | 30 | MU/l |
| CaCl$_2$ | 5 | 5 | 5 | mmol/l |
| POD | 36 | — | 36 | KU/l |
| DA-64 (Wako Pure Chemical Industries, Ltd.) | 81 | 81 | — | μmol/l |

(Measurement Method)

13 μl of the sample and 76 μl of the first reagent were mixed together, and the resultant mixture was incubated at 37° C. for 5 minutes. Then, 28 μl of the second reagent further was added, and the resultant mixture was incubated at 37° C. for 10 minutes. Thereafter, the absorbance of the mixture at a wavelength of 751 nm was measured with the above-described autoanalyzer. The results are shown in Table 4 below.

TABLE 4

|  |  | EXAMPLE | | |
|---|---|---|---|---|
|  |  | 2-1 | 2-2 | 2-3 |
|  | First reagent | 2-1 | 2-2 | 2-3 |
|  | Second reagent | 2-1 | 2-2 | 2-3 |
| Absorbance | Low concentration | 0.010 | 0.011 | 0.013 |
|  | Intermediate concentration | 0.015 | 0.015 | 0.017 |
|  | High concentration | 0.018 | 0.018 | 0.020 |

As shown in Table 4, the reagent kit according to Example 2-1 in which the POD and the color-developing substrate were contained in the first reagent, the reagent kit according Example 2-2 in which the color-developing substrate was contained in the second reagent, and the reagent kit according to Example 2-3 in which the POD was contained in the second reagent and the color-developing substrate was contained in the first reagent exhibited similar results, namely, all the reagent kits exhibited an increase in absorbance in keeping with the HbA1c (%) in the sample.

INDUSTRIAL APPLICABILITY

As described above, according to the measurement method of the present invention, even in the case where a sample contains a non-analyte glycated amine that can react with a FAOD, it is possible to remove the influence of the non-analyte glycated amine sufficiently, thus realizing accurate measurement of a glycated amine. In particular, although conventional measurement methods generally require three or more treatment steps to remove a non-analyte glycated amine, the measurement method of the present invention requires only two treatment steps as described above, but the ability of removing an influence of the non-analyte glycated amine of the method of the present invention is much more excellent than those of the conventional methods. Accordingly, by applying the method of the present invention to, for example, the measurement of glycated Hb in erythrocytes, the measurement can be carried out with higher measurement accuracy than in conventional methods, which further increases the importance of the glycated Hb as an indicator in the diagnosis and the like of diabetes.

The invention claimed is:

1. A method of reducing an influence of a non-analyte glycated amine during a determination of an amount of a glycated protein as an analyte, comprising:
   (a) pretreating a sample by adding a first fructosyl amino acid oxidase (FAOD) to the sample so that the first FAOD acts on a non-analyte glycated amine that is present in the sample and different from a glycated protein as an analyte, thereby reducing an influence of the non-analyte glycated amine on a determination of an amount of the glycated protein as the analyte;
   (b) adding a protease to the sample, thereby degrading the glycated protein as the analyte contained in the sample with the protease;
   (c) after step (b), causing a redox reaction to occur without performing either of the following: (1) adding an additional amount of the first FAOD, and (2) adding a second FAOD that is different from the first FAOD, or a separate FAOD so that in the redox reaction, the first FAOD added in the pretreatment acts on the degradation product of the glycated protein; measuring the redox reaction; and determining the amount of the glycated protein based on a result of the measurement of the redox reaction.

2. The method according to claim 1, wherein the step of adding the protease, the step of causing the redox reaction, and the step of measuring the redox reaction are performed at the same time.

3. The method according to claim 1, wherein the step of causing the redox reaction is a step of causing the FAOD to act on the degradation product of the glycated protein to generate hydrogen peroxide.

4. The method according to claim 3, wherein the step of measuring the redox reaction comprises a step of adding an oxidase and a substrate that develops color by oxidation to the sample so that a reaction between the generated hydrogen peroxide and the substrate is caused by the oxidase.

5. The method according to claim 4, wherein the step of adding the protease, the step of causing the redox reaction, and the step of measuring the redox reaction are performed at the same time by adding the protease, the oxidase, and the substrate that develops color by oxidation to the sample at the same time after pretreating the sample.

6. The method according to claim 4, wherein the step of adding the protease, the step of causing the redox reaction, and the step of measuring the redox reaction are performed at the same time after pretreating the sample by adding the oxidase to the sample together with the FAOD prior to the step of adding the protease and further adding the protease and the substrate that develops color by oxidation to the sample at the same time.

7. The method according to claim 4, wherein the step of adding the protease, the step of causing the redox reaction, and the step of measuring the redox reaction are performed at the same time after pretreating the sample by adding the substrate that develops color by oxidation to the sample together with the FAOD prior to the step of adding the protease and further adding the protease and the oxidase to the sample at the same time.

8. The method according to claim 4, wherein the oxidase is peroxidase.

9. The method according to claim 1, wherein the FAOD is an enzyme specific for a glycated α-amino group of an amino acid residue, an enzyme specific for a glycated side chain of an amino acid residue, or an enzyme specific for both a glycated α-amino group of an amino acid residue and a glycated side chain of an amino acid residue.

10. The method according to claim 1, wherein the non-analyte glycated amine is a glycated amino acid.

11. The method according to claim 1, wherein the glycated amine as the analyte is a glycated peptide or a glycated protein.

12. The method according to claim 1, wherein the glycated amine as the analyte is a glycated amine present in a blood cell.

13. The method according to claim 1, wherein the glycated amine as the analyte is glycated hemoglobin.

14. The method according to claim 1, wherein a tetrazolium compound further is added to the sample prior to the step of adding the protease.

15. The method according to claim 14, wherein the tetrazolium compound comprises 2-(4-iodophenyl)-3-(2,4-dinitrophenyl)-5-(2,4-disulfophenyl)-2H-tetrazolium or a salt thereof.

16. The method according to claim 1, wherein a surfactant further is added to the sample prior to the step of adding the protease.

17. The method according to claim 16, wherein the surfactant is at least one surfactant selected from nonionic surfactants, anionic surfactants, and cationic surfactants.

18. A reagent kit to be used in the method according to claim 1, the reagent kit comprising a first reagent and a second reagent,
wherein the first reagent contains at least a fructosyl amino acid oxidase (FAOD),
the second reagent contains at least a protease, and
one of a peroxidase and a substrate that develops color by oxidation is contained in the first reagent whereas the other is contained in the second reagent, or both the peroxidase and the substrate are contained in the second reagent.

19. The reagent kit according to claim 18, wherein the first reagent further contains a tetrazolium compound.

20. The reagent kit according to claim 19, wherein the tetrazolium compound comprises 2-(4-iodophenyl)-3-(2,4-dinitrophenyl)-5-(2,4-disulfophenyl)-2H-tetrazolium or a salt thereof.

21. The reagent kit according to claim 19, wherein the first reagent further contains a surfactant.

* * * * *